United States Patent
Fukuju et al.

(10) Patent No.: US 9,889,443 B2
(45) Date of Patent: Feb. 13, 2018

(54) SAMPLE ANALYZER AND SAMPLE ANALYZING METHOD

(71) Applicant: Sysmex Corporation, Kobe-shi, Hyogo (JP)

(72) Inventors: Toshikatsu Fukuju, Kobe (JP); Masanori Imazu, Kobe (JP); Masaki Shiba, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 246 days.

(21) Appl. No.: 14/669,840

(22) Filed: Mar. 26, 2015

(65) Prior Publication Data

US 2015/0273464 A1    Oct. 1, 2015

(30) Foreign Application Priority Data

Mar. 28, 2014  (JP) ................................. 2014-067669

(51) Int. Cl.
*G01N 35/10*   (2006.01)
*B01L 3/00*    (2006.01)
(Continued)

(52) U.S. Cl.
CPC ................. *B01L 3/50* (2013.01); *B01L 3/527* (2013.01); *B01L 7/00* (2013.01); *B01L 9/00* (2013.01);
(Continued)

(58) Field of Classification Search
None
See application file for complete search history.

(56) References Cited

U.S. PATENT DOCUMENTS

2008/0240995 A1* 10/2008 Murakami ............. G01N 35/02
                                                        422/82.05
2011/0076774 A1*  3/2011 Mototsu ................. G01N 35/04
                                                        436/43
(Continued)

FOREIGN PATENT DOCUMENTS

CN     102033134 A    4/2011
CN     102171575 A    8/2011
(Continued)

OTHER PUBLICATIONS

Office Action, and English language translation thereof, in corresponding Japanese Application No. 2014-067669, dated Nov. 15, 2016, 7 pages.

*Primary Examiner* — Rebecca L Martinez
(74) *Attorney, Agent, or Firm* — Brinks Gilson & Lione (57) ABSTRACT

A sample analyzer including a reagent reservoir configured to store a plurality of reagent containers; a first reagent dispenser configured to aspirate reagent of a first type from the reagent reservoir and dispense the aspirated reagent into a reaction container disposed at a first dispensing position; a second reagent dispenser configured to aspirate reagent of a second type from the reagent reservoir and dispense the aspirated reagent into a reaction container disposed at a second dispensing position; and a support member configured to support the first and the second reagent dispensers; wherein the first and the second reagent dispensers are supported by the support member so as to be movable independently of each other between each dispensing position and the reagent reservoir is disclosed. A sample analyzing method executed by a sample analyzer is also disclosed.

13 Claims, 5 Drawing Sheets

(51) Int. Cl.
    *B01L 7/00*          (2006.01)
    *B01L 9/00*          (2006.01)
    *G01N 33/53*        (2006.01)
    *B01L 9/06*          (2006.01)

(52) U.S. Cl.
    CPC ..... *G01N 33/5302* (2013.01); *G01N 33/5304* (2013.01); *G01N 35/1002* (2013.01); *B01L 9/06* (2013.01); *B01L 2300/06* (2013.01)

(56) References Cited

U.S. PATENT DOCUMENTS

2012/0230873 A1\* 9/2012 Yanami .............. G01N 35/0092
                                                              422/64
2013/0288355 A1    10/2013  DeWitte et al.

FOREIGN PATENT DOCUMENTS

| CN | 103370627 A | 10/2013 |
|----|----|----|
| EP | 1 460 432 A1 | 9/2004 |
| JP | 62-153574 U | 9/1987 |
| JP | S62-287161 A | 12/1987 |
| JP | H03-057961 A | 3/1991 |
| JP | H06-324058 A | 11/1994 |
| JP | H11-304818 A | 11/1999 |
| JP | 2004-279356 A | 10/2004 |
| JP | 2008-170332 A | 7/2008 |
| JP | 2008-180538 A | 8/2008 |
| JP | 2008-209339 A | 9/2008 |
| JP | 2009-145188 A | 7/2009 |
| JP | 2010-107308 A | 5/2010 |

\* cited by examiner

SAMPLE ANALYZER AND SAMPLE ANALYZING METHOD

RELATED APPLICATIONS

This application claims priority from prior Japanese Patent Application No. 2014-067669, filed on Mar. 28, 2014, entitled "SAMPLE ANALYZER", the entire contents of which are incorporated herein by reference.

BACKGROUND OF THE INVENTION

1. Field of the Invention

The present invention relates to a sample analyzer and sample analyzing method.

2. Description of the Related Art

Japanese Patent Publication Application No. 2008-209339 discloses a sample analyzer incorporating a first reagent dispenser configured to aspirate reagent from a reagent disk and dispense the aspirated reagent into a reaction vessel disposed at a first dispensing position, and a second reagent dispenser configured to aspirate reagent form a reagent disk and dispense the aspirated reagent to a reaction vessel disposed at a second dispensing position. In this sample analyzer, the first reagent dispenser is supported by a first support member, and the second reagent dispenser is supported by a second support member. The first support member and the second support member are arranged at an interval.

In Japanese Patent Publication Application No. 2008-209339, the sample analyzer is enlarged because the first support member and the second support member are arranged at an interval.

SUMMARY OF THE INVENTION

The scope of the present invention is defined solely by the appended claims, and is not affected to any degree by the statements within this summary.

The sample analyzer of one aspect of the present invention has a reagent reservoir configured to store a plurality of reagent containers; a first reagent dispenser configured to aspirate reagent of a first type from the reagent reservoir and dispense the aspirated reagent into a reaction container disposed at a first dispensing position; a second reagent dispenser configured to aspirate reagent of a second type from the reagent reservoir and dispense the aspirated reagent into a reaction container disposed at a second dispensing position; and a support member configured to support the first and the second reagent dispensers; wherein the first and the second reagent dispensers are supported by the support member so as to be movable independently of each other between each dispensing position and the reagent reservoir.

The sample analyzer of one aspect of the present invention has a reagent reservoir configured to store a plurality of reagent containers; a first reagent dispenser configured to aspirate reagent containing magnetic particles as a reagent of a first type from the reagent reservoir and dispense the aspirated reagent into a reaction container disposed at a first dispensing position; a BF separator configured to remove the unreacted component in the sample accommodated in the reaction container containing the dispensed reagent of the first type; a second reagent dispenser configured to aspirate reagent of a second type from the reagent reservoir and dispense the aspirated reagent into a reaction container from which the unreacted component has been removed by the BF separator at the second dispensing position; and a support member configured to support the first and the second reagent dispensers; wherein the first and the second reagent dispensers are supported by the support member so as to be movable independently of each other between each dispensing position and the reagent reservoir.

The sample analyzing method executed by a sample analyzer of one aspect of the present invention has moving a first reagent dispenser which has aspirated reagent of a first type from a reagent reservoir from the reagent reservoir to a first dispensing position, and dispensing the aspirated reagent of the first type into a reaction container set at a first dispensing position, wherein the first reagent dispenser is supported by a support member provided in the sample analyzer; moving a second reagent dispenser which has aspirated reagent of a second type from a reagent reservoir from the reagent reservoir to a second dispensing position, and dispensing the aspirated reagent of the second type into a reaction container set at a second dispensing position, wherein the second reagent dispenser is supported by the support member.

DETAILED DESCRIPTION OF THE PREFERRED EMBODIMENTS

The structure of the analyzer 100 of an embodiment of the present invention is described below with reference to FIGS. 1 through 5.

The sample analyzer 100 is an immunoanalyzer configured to immunologically examine items including infectious diseases such as HIV, hepatitis B virus and the like, tumor markers, and thyroid hormone using clinical samples such as blood collected from a subject. The sample analyzer 100 quantitatively or qualitatively measures antibodies or antigen contained in a serum sample to be measured. When performing quantitative measurement of antigen contained in a sample, the sample analyzer 100 mixes the sample and magnetic particles sensitized by a capture antibody to form a complex of antigen and magnetic particles in the sample, and remove the unreacted component in the sample using the first order BF separator 12. The sample analyzer 100 then mixes a labeling antibody with the sample containing the complex, and removes the unreacted labeling antibody in the sample using a second order BF separator 14. The sample analyzer 100 then adds a dispersion liquid and luminescent substrate to the sample, and measures the amount of light produced through the reaction of the luminescent substrate and the enzyme bound to the labeling antibody.

[Structure of the Sample Analyzer 100]

Figure 1:
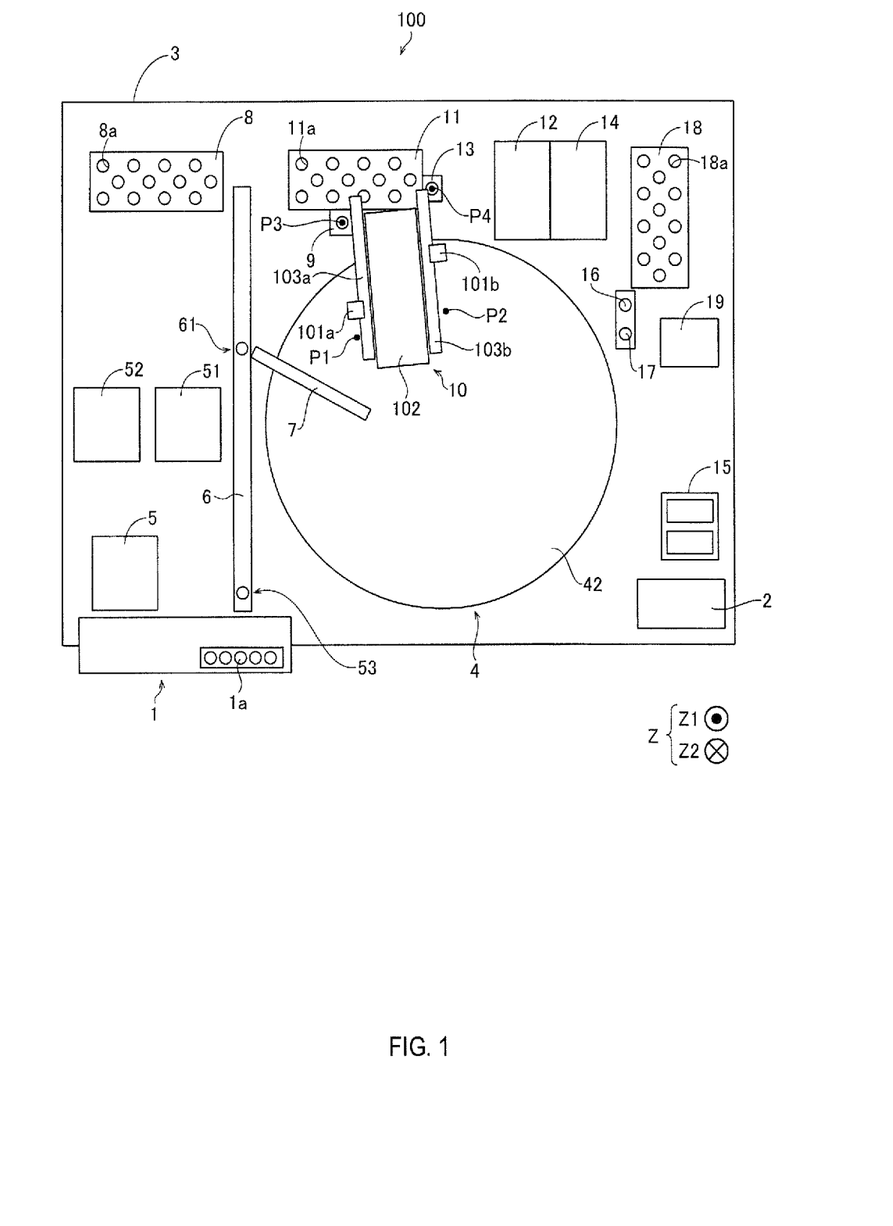
FIG. 1 is a schematic view showing the sample analyzer of the embodiment.

The sample analyzer 100 has a sample transporting part 1, control device 2, and measuring device 3, as shown in FIG. 1.

The control device 2 is configured by a personal computer. Specifically, the control device 2 includes a CPU (not shown in the drawing), a display unit, a memory unit and the like. The control device 2 controls the measuring device 3 to perform measurements based on a user input measurement order. The memory unit stores reagent information and position information for the R2 reagent container 50 and R1-R3 reagent containers 60, which are described later. The memory unit also stores programs through which the CPU controls the operations of the sample transporting part 1 and the measuring device 3. The operations of the sample transporting part 1 and the measuring device 3 which are described below are executed under the control of the CPU when the COU of the control device 2 executes the program stored in the memory unit.

The sample transporting part 1 moves a plurality of test tubes 1a containing samples to the sample aspirating position of the sample dispenser 5, which is described later.

The measuring device 3 is mainly configured by a container supplier 51, pipette supplier 52, reagent reservoir 4, sample dispenser 5, sample transport rail 6, first reagent dispensing arm 7, first reactor 8, first support 9, dispensing device 10, second reactor 11, primary BF separator 12, second support 13, secondary BF separator 14, R4/R5 reagent mounting part, fourth reagent dispenser 16, fifth reagent dispenser 17, third reactor 18, and photometric unit 19.

The container supplier 51 supplies reaction containers 30 to a sample discharge position 53. The sample dispenser 5 includes a nozzle which is not shown in the drawing, and a pipette supplied from the pipette supplier 52 is installed on the leading end of the nozzle. The sample dispenser 5 aspirates the sample contained in the rest tube 1a when the test tube 1a has been moved to the sample aspirating position by the sample transporting part 1, and dispenses the aspirated sample into a reaction container 30 which is disposed at the sample discharge position 53.

The sample transport rail 16 extends linearly from the sample discharge position 53 toward the first reactor 8. The sample transport rail 6 moves the reaction container 30 from the sample discharge position 53 toward the first reactor 8. R1 reagent is dispensed by the R1 reagent dispensing arm 7 into the reaction container 30 at an R1 reagent dispensing position 61 midway as the reaction container 30 moves to the first reactor 8. The R1 reagent is a buffer solution.

The first reactor 8 is provided with a plurality of holders 8a for accommodating a plurality of reaction containers 30. The first reactor 8 has the function of heating the reaction container 30. The reaction container 30 is moved to the endpoint by the sample transport rail 6, then taken up by a catcher (not shown in the drawing) and installed in one of the holders 8a of the first reactor 8. The reaction container 30 is heated to a predetermined temperature for a predetermined time by the first reactor 8.

After the reaction container 30 has been heated for a predetermined time, the reaction container 30 is removed from the first reactor 8 by a catcher which is not shown in the drawing, and subsequently installed in the first support 9. The first reagent dispenser 101a of the dispensing device 10 dispenses R2 reagent into the reaction container 30 installed on the first support 9. The R2 reagent is a suspension of magnetic particles sensitized by a capture antibody. The dispensing device 10 is described later.

The second reactor 11 is provided with a plurality of holders 11a for accommodating a plurality of reaction containers 30. The second reactor 11 has the function of heating the reaction container 30. The reaction container 30 containing dispensed R2 reagent is taken up by a catcher which is not shown in the drawing, and installed in one of the holders 11a of the second reactor 11. The reaction container 30 is heated to a predetermined temperature for a predetermined time by the second reactor 11.

After the reaction container 30 has been heated for a predetermined time by the second reactor 11, the reaction container 30 is taken up by a catcher (not shown in the drawing) and installed in the primary BF separator 12. The primary BF separator 12 separates the unreacted component and complex containing magnetic particles in the sample contained in the reaction container 30 using a magnet, and removes the unreacted component.

The reaction container 30 which has been processed by the primary BF separator 12 is then taken up by a catcher which is not shown in the drawing, and installed in the second support 13. The second reagent dispenser 101b of the dispensing device 10 dispenses R3 reagent into the reaction container 30 installed on the second support 13. The R3 reagent is a liquid containing labeled antibody (hereinafter referred to as labeled antibody). The reaction container 30 containing the dispensed R3 reagent is taken up by a catcher (not shown in the drawing), installed in the second reactor 11 and heated for a predetermined time.

After the reaction container 30 has been heated for a predetermined time by the second reactor 11, the reaction container 30 is taken up by a catcher (not shown in the drawing) and installed in the secondary BF separator 14. The secondary BF separator 14 separates the unreacted labeled antibody contained in the R3 reagent and complex containing magnetic particles in the sample contained in the reaction container 30 using a magnet, and removes the unreacted labeled antibody.

The reaction container 30 which has been processed by the secondary BF separator 14 is then taken up by a catcher which is not shown in the drawing, and installed in the fourth reagent dispenser 16. The fourth reagent dispenser 16 dispenses R4 reagent into the installed reaction container 30. The R4 reagent is a dispersion liquid.

After the R4 reagent has been dispensed to the reaction container 30 by the fourth reagent dispenser 16, the reaction container 30 is taken up by a catcher (not shown in the drawing) and installed in the first reagent dispenser 17. The fifth reagent dispenser 17 dispenses R5 reagent into the installed reaction container 30. The R5 reagent is a liquid containing luminescent substrate which reacts with the enzyme of the labeled antibody and produced light.

The third reactor 18 is provided with a plurality of holders 18a for accommodating a plurality of reaction containers 30. The reaction container 30 containing dispensed R5 reagent is taken up by a catcher which is not shown in the drawing, and installed in one of the holders 18a of the third reactor 18. The reaction container 30 is heated to a predetermined temperature for a predetermined time by the third reactor 18.

After the reaction container 30 has been heated for a predetermined time by the third reactor 18, the reaction container 30 is taken up by a catcher (not shown in the drawing) and moved to the photometric unit 19. The photometric unit 19 measures the light given off from the reaction container 30. After the photometric measurement, the reaction container 30 is discarded and the measurement ends.

[Reagent Reservoir 4]

Figure 2:
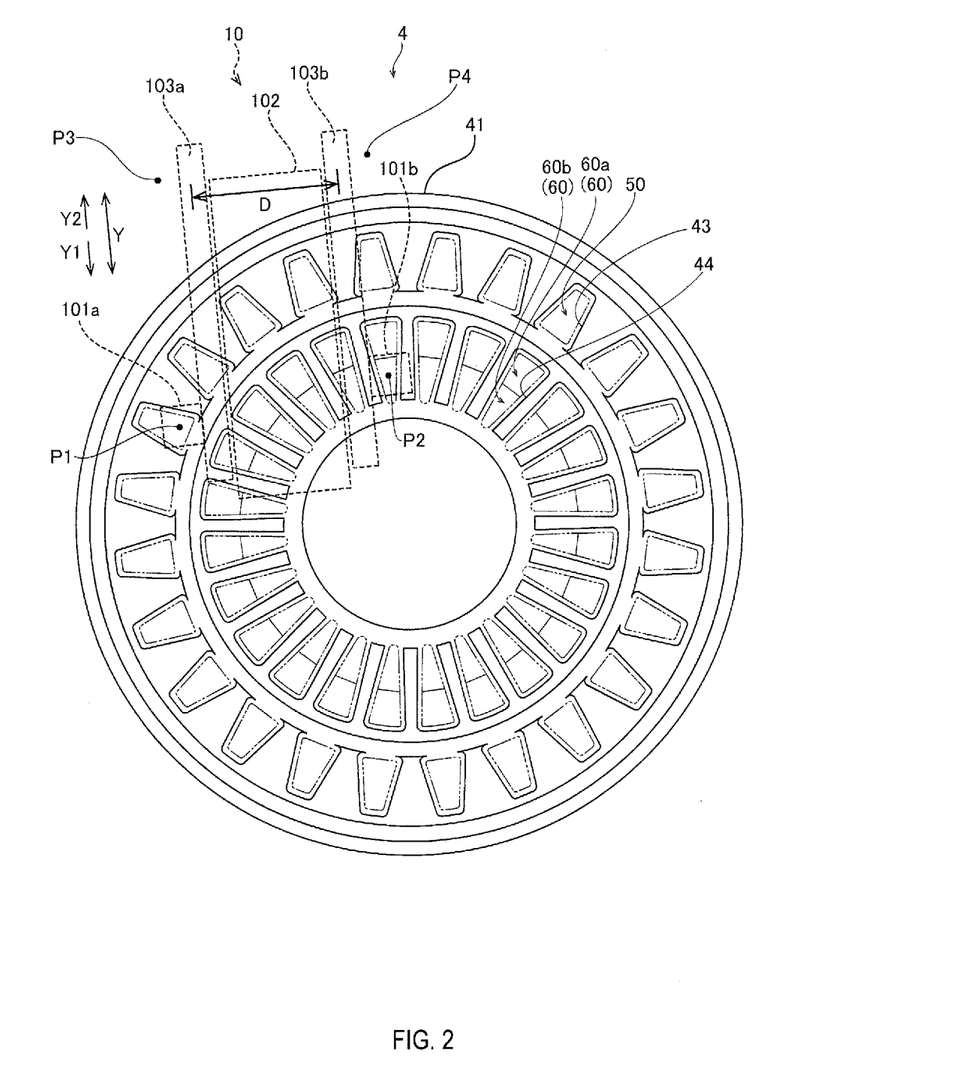
FIG. 2 is a schematic view showing the reagent reservoir of the embodiment.

The positional relationship between the reagent reservoir 4 and the dispensing device 10 is described with reference to FIG. 2. The reagent reservoir 4 includes a substantially cylindrical housing 41, and a cover part 42 which covers the housing 41 from the Z1 side (refer to FIG. 1). The reagent reservoir 4 includes a plurality of outside housings 43 and a plurality of inside housings 44 which are circularly arranged in the center area of the housing 41. The plurality of outside housings 43 are arranged on the outer side of the inside housings 44 in the radial direction of the reagent reservoir 4. The outside housings 43 house the R2 reagent containers 50. The R2 reagent containers 50 contain R2 reagent. The plurality of inside housings 44 are arranged on the inner side of the outside housings 43 in the radial direction of the reagent reservoir 4. The inside housings 44 house R1/R3 reagent containers 60. The R1 reagent containers contain R1 reagent. The R3 reagent containers contain R3 reagent. The R1/R3 reagent containers 60 are divided into an R1 reagent housing part 60a and an R3 reagent housing part 60b in the outside direction of the radius. The outside housing 43 and the inside housing 44 are configured to be rotatable independently of each other with the center of the reagent reservoir 4 as the axis.

The reagent reservoir 4 is configured so that the R2 reagent container 50 to be aspirated is placed directly below the position P1 where the first reagent dispenser 101a aspirates the R2 reagent by rotating the outside housing 43. The reagent reservoir 4 also is configured so that the R3 reagent container 60b to be aspirated of the R3 reagent container 60 is placed directly below the position P2 where the second reagent dispenser 101b aspirates the R3 reagent by rotating the inside housing 44. These operations are controlled by the control device 2. Specifically, the control device 2 specifies one of the R2 reagent containers 50 to be aspirated according to the measurement item from among the plurality of R2 reagent containers 50 based on the measurement item contained in the measurement order. The control device 2 also specifies one of the R3 reagent containers 60 to be aspirated according to the measurement item from among the plurality of R3 reagent containers 60 based on the measurement item contained in the measurement order. The control device 2 controls the reagent reservoir 4 so as to position the specified R2 reagent container 50 and R3 reagent container 60 are position P1 and position P2, respectively. Openings not shown in the drawing are formed in the cover 42 at the position P1 where the R2 reagent is to be aspirated and the position P2 where the R3 reagent is to be aspirated.

[Dispensing Device 10]

The structure of the dispensing device 10 is described with reference to FIG. 3. The dispensing device 10 is mainly configured by a support member 102, first guide member 103a and second guide member 103b which fixedly support the support member 102, a first reagent dispenser 101a engaged with the first guide member 103a so as to be horizontally movable, and second reagent dispenser 101b engaged with the second guide member 103b so as to be horizontally movable.

Figure 3:
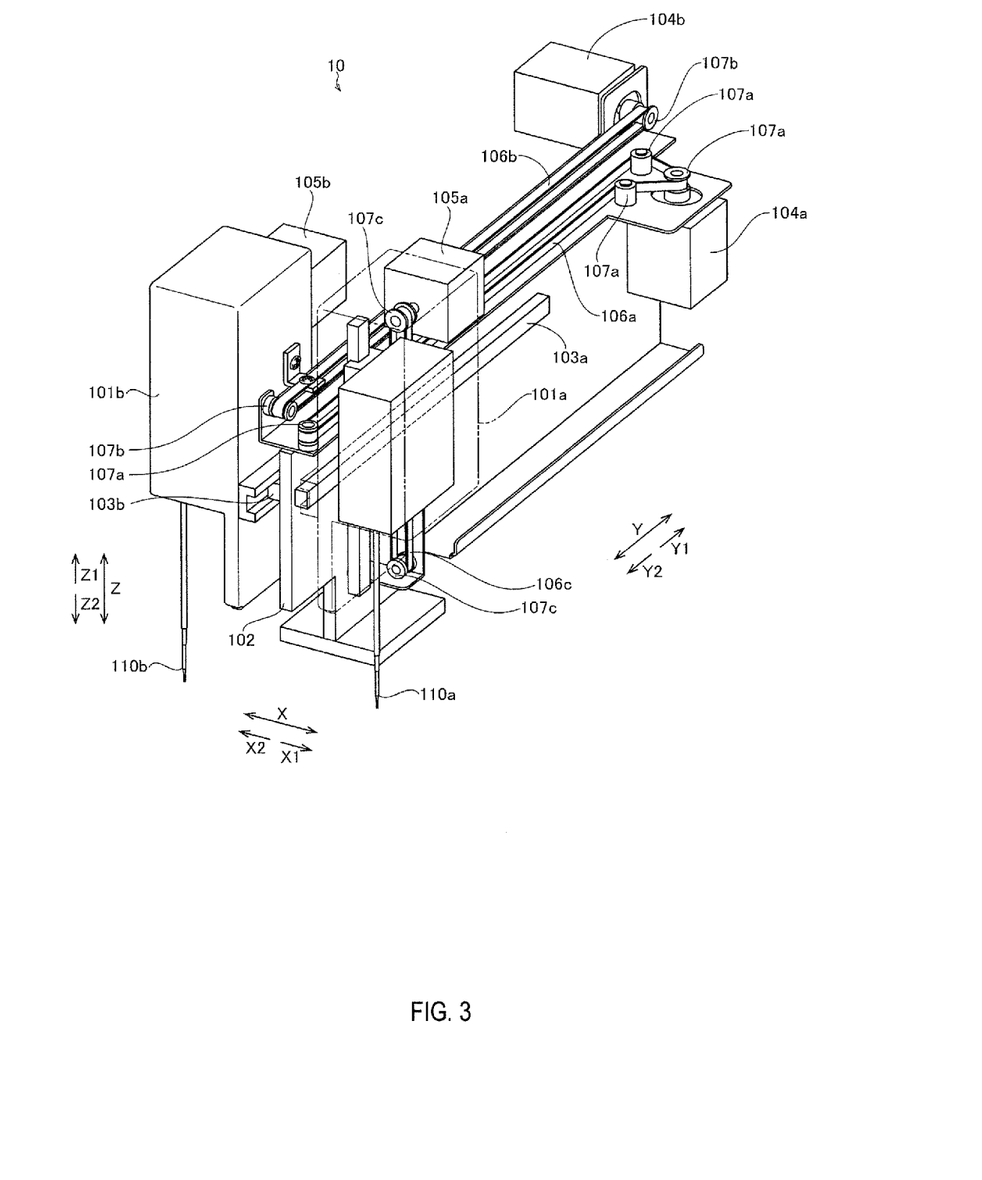
FIG. 3 is a perspective view showing the first reagent dispenser, second reagent dispenser, and support member of the embodiment.

As shown in FIG. 3, the first reagent dispenser 101a and the second reagent dispenser 101b are supported by the shared support member 102. In this way the sample analyzer 100 can be made more compact compared to a conventional apparatus in which the respective reagent dispensers are supported by separate support members. The first reagent dispenser 101a and the second reagent dispenser 101b engage the guide member separately, and are movable independent of each other. The two reagent dispensers therefore can aspirate and dispense reagent without interfering with each other.

The support member 102 is formed by a metal plate extending substantially in the vertical direction. The first guide member 103a linearly extending along the Y-axis, that is, horizontally, is mounted on the side in the X1 direction of the support member 102. The first reagent dispenser 101a engages the first guide member 103a so as to be slidable.

The second guide member 101b linearly extending horizontally along the Y-axis is mounted on the backside of the side on which the first guide member 101a is mounted, that is, on the side in the X2 direction of the support member 102. The second reagent dispenser 101b engages the second guide member 103b so as to be slidable.

The analyzer is made more compact and the interval of the two guide members is reduced in the present embodiment by sharing the support member 102 which supports the two reagent dispensers, and providing the guide members 103a and 103b on both sides of the support member to guide the movement of the two reagent dispensers.

A pair of motors 104a and 104b, a pair of belts 106a and 106b, and a plurality of pulleys and 107a and 107b are mounted on the support member 102.

The motor 104a generates a drive force to move the first reagent dispenser 101a horizontally. A shaft rotated by the motor 104a is connected to one among the plurality of pulleys 107a. The belt 106a is looped around the plurality of pulleys 107a. The first reagent dispenser 101a is fixedly attached to the belt 106a. When the motive force of the motor 104a is transmitted through the belt 106a and pulleys 107a, the first reagent dispenser 101a moves linearly in the Y1 direction or Y2 direction along the first guide member 103a.

The motor 104b moves the second reagent dispenser 101b horizontally. The motor 104b, belt 106b, and pulleys 107b are connected the same as the motor 104a, belt 106a, and pulleys 107a described above. When the motive force of the motor 104b is transmitted through the belt 106b and pulleys 107b, the second reagent dispenser 101b moves linearly in the Y1 direction or Y2 direction along the second guide member 103b.

The first reagent dispenser 101a is provided with a pipette 110a. The first reagent dispenser 101a aspirates the R2 reagent from the R2 reagent container at position P1 through the pipette 110a, and dispenses the aspirated R2 reagent into the reaction container 30 at the first dispensing position P3.

FIG. 3 shows the perspective of the interior of the first reagent dispenser 101a. A belt 106c and a pair of pulleys 107c are provided on the inside of the first reagent dispenser 101a. A motor 105a is mounted on the first reagent dispenser 101a, and generates a drive force to vertically move the pipette 110a. When the motor 105a is actuated, the motive force is transmitted through the belt 106c and pair of pulleys 107c to the pipette 110a. The pipette 110a therefore is lifted and lowered along the Z-axis.

The second reagent dispenser 101b is provided with a pipette 110b. The second reagent dispenser 101b aspirates the R3 reagent from the R3 reagent container at position P2 through the pipette 110b, and dispenses the aspirated R3 reagent into the reaction container 30 at the second dispensing position P4.

A vertical movement device identical to that of the first reagent dispenser 101a is provided inside the second reagent dispenser 101b, and the pipette 110b is lifted and lowered along the Z-axis by the actuation of the motor 105b mounted on the second reagent dispenser 101b.

The first reagent dispenser 101a can access the reaction container 30 and access the R2 reagent container of the reagent reservoir 4 by moving on the two axes of linear horizontal movement and linear vertical movement alone. Similarly, the second reagent dispenser 101b can access the reaction container 30 and access the R3 reagent container of the reagent reservoir 4 by moving on the two axes of linear horizontal movement and linear vertical movement alone. A motor is not required to rotate the pipette since reagent aspiration and dispensing are executed only by the linear movement on two axes. The analyzer can be made more compact and the range of movement of the pipette is reduced within the analyzer compared to configurations in which the pipette is rotated.

Other Embodiments

Note that the embodiment of the present disclosure is an example in all aspects and not to be considered limiting in any way. The scope of the present invention is expressed by the scope of the claims and not by the description of the embodiment, and includes all meanings and equivalences and modifications pertaining thereunto.

Figure 4:
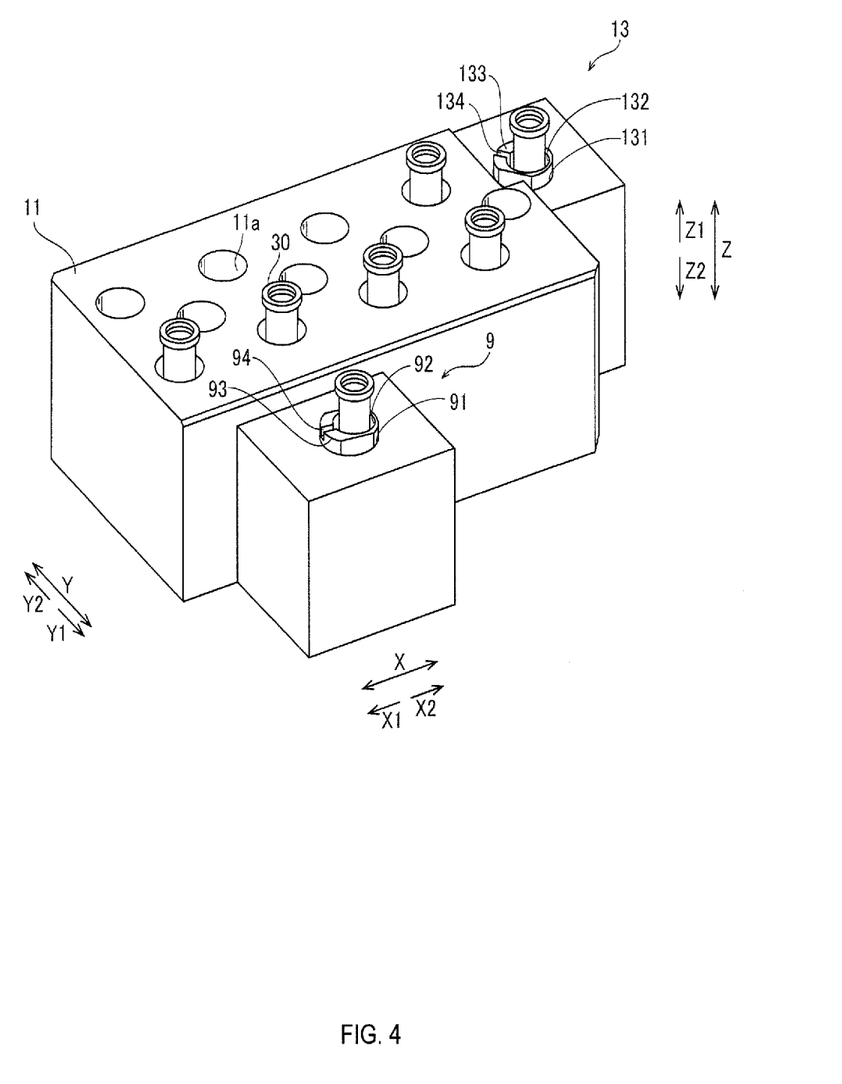
FIG. 4 shows the first support member and the second support member of the sample analyzer of another embodiment.
Figure 5:
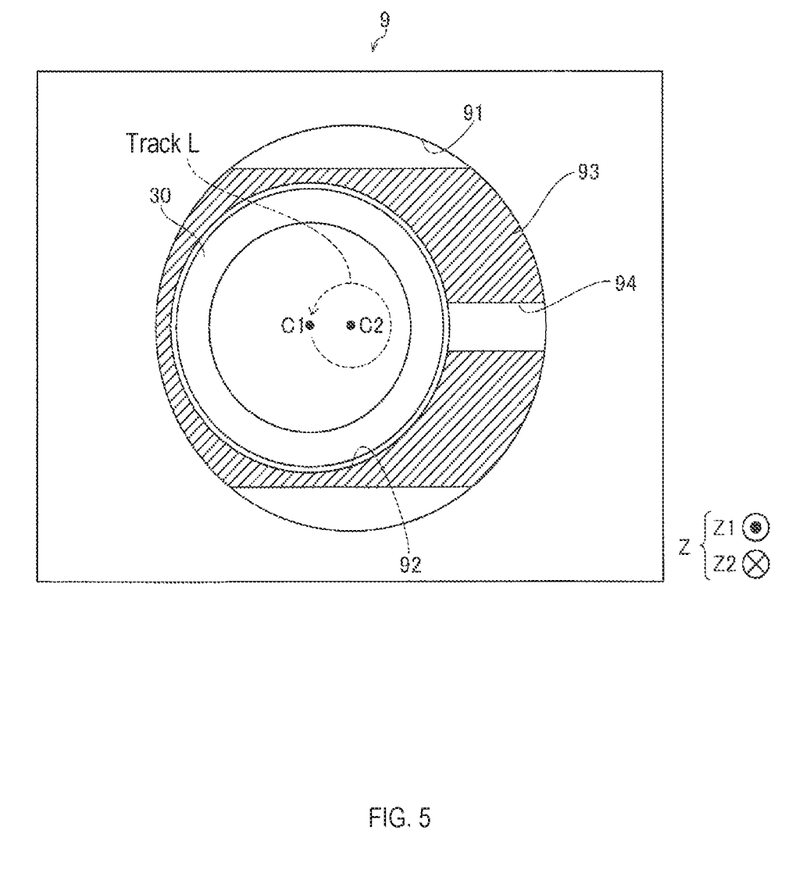
FIG. 5 is a plan view showing the regulating member of another embodiment.

As shown in FIG. 4, the first support 9 and the second support 13 also may be provided with a regulating member to regulate the position of the reaction container 30. FIG. 5 shows an example of a regulating member. A hole 91 is provided in the first support 9. The hole 91 is substantially circular in planar view. A regulating member 93 is provided in the hole 91. A notch 94 and a retaining hole 92 having an internal diameter sufficient to insert the reaction container 30 are formed in the regulating member 93. The regulating member 93 is configured to be rotatable along the inside of the circle of the hole 91. In FIG. 5, the regulating member 93 is denoted by hatching for convenience. A regulating member 133 having an identical structure also is provided on the second support 13.

The center position C1 of the reaction container 30 inserted in the retaining hole 92 is eccentric to the center position C2 of the hole 91 in planar view. The center position C1 of the reaction container 30 can be moved so as to describe a track L by inserting a tool into the notch 94 and rotating the regulating member 93. In this way, the center position C1 of the reaction container 30 can be regulated.

According to this configuration, the position of insertion of the pipette 110a into the reaction container 30 by the first reagent dispenser 101a can be regulated by rotating the regulating member 93. A high degree of accuracy in assembly is required to support the two reagent dispenser on a shared support member 102 so that the respective reagent dispensers can access the reagent container and the reaction container on both sides by movement on the horizontal and vertical two axes alone. That is, the direction of the support member 102 must be regulated so that the first position P1 and the third position P3 are on a straight line, and the second position P2 and the fourth position P4 are on a straight line.

Support member 102 mounting errors are absorbed by the regulating member 93 since using the regulating member 93 regulates the center position of the reaction container 30 matching the direction of the support member 102 without matching the direction of the support member 102 to the positions P3 and P4 of the reaction container 30.

Note that although the example shows the regulating member provided for both position P3 and position P4, the regulating member also may be provided for only one or the other position P3 or position P4.

Although the above embodiment is described in terms of an immunoanalyzer configured to examine serum as an example of the sample analyzer, the present invention is also applicable to biochemical analyzers, urine analyzers, and genetic testing apparatuses.

Although the above embodiment is described by way of example in which the support member supports both a first reagent dispenser and a second reagent dispenser, the present invention is not limited to this configuration. The present invention also is applicable to a support member supporting a separate reagent dispenser in addition to the first reagent dispenser and the second reagent dispenser.

What is claimed is:

1. A sample analyzer comprising:
a reagent reservoir configured to store a plurality of reagent containers;
a first reagent dispenser configured to aspirate reagent of a first type from the reagent reservoir and dispense the aspirated reagent into a reaction container disposed at a first dispensing position;
a second reagent dispenser configured to aspirate reagent of a second type from the reagent reservoir and dispense the aspirated reagent into a reaction container disposed at a second dispensing position; and
a support member having on one side thereof a first guide portion configured to guide the first reagent dispenser so as to linearly move from the reagent reservoir to the first dispensing position, the support member having on the other side thereof a second guide portion configured to guide the second reagent dispenser so as to linearly move from the reagent reservoir to the second dispensing position.

2. The sample analyzer of claim 1, wherein the first guide portion and the second guide portion are provided to the support member such that the first guide portion and the second guide portion face each other.

3. The sample analyzer of claim 1, wherein
the support member is formed by a plate-like member which extends in a substantially vertical direction and which has a one side face and the other side face respectively extending along a horizontal linear movement direction of the first and second reagent dispensers,
the first reagent dispenser is movably mounted to the one side face of the plate-like member having the first guide portion interposed therebetween, and
the second reagent dispenser is movably mounted to the other side face of the plate-like member having the second guide portion interposed therebetween.

4. The sample analyzer of claim 1, wherein
the first reagent dispenser is configured to access the reagent container within the reagent reservoir and access the reaction container by only horizontal linear movement and vertical movement; and
the second reagent dispenser is configured to access the reagent container within the reagent reservoir and access the reaction container by only horizontal linear movement and vertical movement.

5. The sample analyzer of claim 1, further comprising:
a holder configured to hold the reaction container at the first dispensing position,
wherein a retaining hole having an internal diameter sufficient for the insertion of at least one reaction container is formed in the holder; and
the retaining hole comprises a regulating member configured to regulate the center position of the inserted reaction container.

6. The sample analyzer of claim 5, wherein
the regulating member is configured to hold the reaction container so that the center position of the reaction container is eccentric to the retaining hole.

7. The sample analyzer of claim 1, wherein
the reagent reservoir comprises: a plurality of outside housings arranged circularly to hold reagent containers containing the reagent of the first type; and a plurality of inside housings provided inside the outside housings and arranged circularly to hold reagent containers containing the reagent of the second type, and
the outside housings and the inside housings are configured to be rotatable independently of each other on the same axis.

8. A sample analyzer comprising:
a reagent reservoir configured to store a plurality of reagent containers;
a first reagent dispenser configured to aspirate reagent of a first type from the reagent reservoir and dispense the aspirated reagent into a reaction container disposed at a first dispensing position;
a second reagent dispenser configured to aspirate reagent of a second type from the reagent reservoir and dispense the aspirated reagent into a reaction container disposed at a second dispensing position; and
a support member configured to support the first and second reagent dispensers, wherein
the first and second reagent dispensers are supported by the support member so as to be movable independently of each other between each dispensing position and the reagent reservoir,
the support member comprises a first guide portion configured to guide the movement of the first reagent dispenser between the first dispensing position and the reagent reservoir, and a second guide portion configured to guide the movement of the second reagent dispenser between the second dispensing position and the reagent reservoir, and
the first guide portion and the second guide portion are provided to the support member such that the first guide portion and the second guide portion face each other.

9. The sample analyzer of claim 1, wherein
the support member is formed so as to extend along the direction in which the first and second reagent dispensers linearly move.

10. The sample analyzer of claim 1, wherein
the first reagent dispenser is supported by the support member so as to be linearly movable between the first dispensing position and a first aspirating position for the reagent of the first type in the reagent reservoir, and
the second reagent dispenser is supported by the support member so as to be linearly movable between the second dispensing position and a second aspirating position of the reagent of the second type in the reagent reservoir.

11. The sample analyzer of claim 1, wherein
the reagent of the first type and the reagent of the second type are different in type from each other, and
the reagent of the second type is configured to be dispensed after the reagent of the first type has been dispensed.

12. The sample analyzer of claim 1, wherein
the first reagent dispenser and the second reagent dispenser are configured to be able to access the reagent reservoir commonly used thereby.

13. A sample analyzer comprising:
a reagent reservoir configured to store a plurality of reagent containers;
a first reagent dispenser configured to aspirate reagent of a first type from the reagent reservoir and dispense the aspirated reagent into a reaction container disposed at a first dispensing position;
a second reagent dispenser configured to aspirate reagent of a second type from the reagent reservoir and dispense the aspirated reagent into a reaction container disposed at a second dispensing position; and
a support member configured to support the first and second reagent dispensers, wherein
the first and second reagent dispensers are supported by the support member so as to be movable independently of each other between each dispensing position and the reagent reservoir,
the sample analyzer further comprises a holder configured to hold the reaction container at the first dispensing position,
a retaining hole having an internal diameter sufficient for the insertion of at least one reaction container is formed in the holder, and
the retaining hole comprises a regulating member configured to regulate the center position of the inserted reaction container.

* * * * *